(12) United States Patent
O'Hare

(10) Patent No.: US 8,709,500 B2
(45) Date of Patent: *Apr. 29, 2014

(54) DRUG DELIVERY SYSTEM

(75) Inventor: Dermot Michael O'Hare, Oxford (GB)

(73) Assignee: Isis Innovation Limited, Oxford (GB)

( * ) Notice: Subject to any disclaimer, the term of this patent is extended or adjusted under 35 U.S.C. 154(b) by 166 days.

This patent is subject to a terminal disclaimer.

(21) Appl. No.: 12/821,990

(22) Filed: Jun. 23, 2010

(65) Prior Publication Data

US 2010/0310613 A1    Dec. 9, 2010

Related U.S. Application Data

(60) Division of application No. 12/011,773, filed on Jan. 28, 2008, which is a continuation of application No. 10/450,101, filed as application No. PCT/GB01/05484 on Dec. 12, 2001, now abandoned.

(30) Foreign Application Priority Data

Dec. 14, 2000 (GB) .................................. 0030460.0

(51) Int. Cl.
| | | |
|---|---|---|
| *A61K 9/00* | (2006.01) | |
| *A61K 9/14* | (2006.01) | |
| *A61K 31/19* | (2006.01) | |
| *A61K 31/192* | (2006.01) | |
| *A61K 31/196* | (2006.01) | |
| *A61K 33/08* | (2006.01) | |
| *A61K 33/10* | (2006.01) | |

(52) U.S. Cl.
CPC . *A61K 9/14* (2013.01); *A61K 31/19* (2013.01); *A61K 31/192* (2013.01); *A61K 31/196* (2013.01); *A61K 33/08* (2013.01); *A61K 33/10* (2013.01)
USPC ........... 424/688; 424/400; 424/489; 424/677; 424/715; 424/717; 424/722; 514/557; 514/567; 514/570

(58) Field of Classification Search
None
See application file for complete search history.

(56) References Cited

U.S. PATENT DOCUMENTS

| | | | |
|---|---|---|---|
| 3,980,685 A | | 9/1976 | Miyata et al. |
| 4,514,389 A | | 4/1985 | Miyata |
| 4,917,883 A | * | 4/1990 | Strobridge ...................... 424/59 |
| 5,453,267 A | | 9/1995 | Kemp et al. |
| 5,474,762 A | * | 12/1995 | Carr et al. ........................ 424/59 |
| 5,674,912 A | * | 10/1997 | Martin ............................. 514/724 |

FOREIGN PATENT DOCUMENTS

| | | | | |
|---|---|---|---|---|
| JP | 48082021 | * | 11/1973 | ............. A61K 31/19 |
| WO | WO00/59629 A1 | | 10/2000 | |

OTHER PUBLICATIONS

Derwent-ACC-No. 1984-013556 abstracting JP 48082021 published Nov. 2, 1973; 3 pages.*
Ansel (Pharmaceutical Dosage forms and Drug Delivery Systems 1999, 7th Edition table of contents; 3 pages).*
Carlino (Solid State Ionics 1997, 98, 73-84).*
Ansel (Pharmaceutical Dosage Forms and Drug Delivery Systems, 7th Edition 1999, pp. 80, 81 and 88).*
Kanzaki et al. "Drug Release Characteristics of Ternary Mica/ Phosphatidylcholine/Drug Intercalation Compounds," Chem. Pharm. Bull., 1998, 46(11):1663-1666.
Makoto et al., "Process for producing anion-layered double hydroxide intercalation compounds and products thus produced," Database CA Online, Chemical Abstracts Service, Columbus Ohio, US, Ogawa, Retrieved from STN Database accession No. 133:313612 HCA.
Borja et al., "Fatty Acids in Layered Metal Hydroixeds: Membrane-Like Structure and Dynamics," J Phys. Chem., 1992, 96(13):5434-5444.
Carlino, "The intercalation of carboxylic acids into layered double hydroxides: a critical evaluation and review of the different methods," Solid State Ionics, 1997, 98(1-2):73-84.
Choy et al., "Intercalative Nanohybrids of Nucleoside Monophosphates and DNA in Layered Metal Hydroxide," J Am. Chem. Soc., 1999, 121(6):1399-1400.
Kanzaki et al. "Drug Release Characteristics of Ternary Mica/ Phosphatidylcholine/Drug Intercalation Compounds," Chem. Pharrn. Bull., 1998, 46(11):1663-1666.
Makoto et al., "Process for producing anion-layered double hydroxide intercalation compounds and products thus produced," Database CA Online, Chemical Abstracts Service, Columbus Ohio, US, Ogawa, Retrieved from STN Database accession No. 133:313612 HCA, Dec. 10, 2000.
Meyn et al., "Anion-Exhange Reactions of Layered Double Hydroxides," Inorg. Chem., 1990, 29(26):S201-S207.
Nakayama et al., "Intercalation of amino acids and peptides into Mg-Al layered double hydroxide by reconstruction method," Int. J Pharm., 2004, 269(2):469-478.
Gschnait et al., "Topical Indomethacin Protects from UVB and UVA Irradiation", Arch Dermatol Res, vol. 276, pp. 131-132 (1984).

* cited by examiner

*Primary Examiner* — Ernst Arnold
(74) *Attorney, Agent, or Firm* — Rudy J. Ng; Bret E. Field; Bozicevic, Field & Francis, LLP

(57) ABSTRACT

A drug delivery system for the controlled release of a pharmaceutically-active compound by oral route comprises an intercalate of a layered double hydroxide having, before intercalation, layers of metal hydroxides, and having intercalated therein a pharmaceutically-active compound having at least one anionic group. A preferred layered double hydroxide is one that has layers which comprise $[LiAl_2(OH)_6]^+$. The drug delivery system has use in the delivery of drugs such as 4-biphenylacetic acid, Diclofenac, Gemfibrozil, Ibuprofen, Naproxen, 2-Propylpentanoic acid and Tolfenamic acid.

20 Claims, 6 Drawing Sheets

FIG. 1 Release profiles for diclofenac at pH 4 and pH 7

Release profiles for gemfibrozil at pH 4 and pH 7

FIG. 4 Release profiles for tolfenamic acid at pH 4 and pH 7

Release profiles for 4-biphenylacetic acid at pH 4 and pH 7

DRUG DELIVERY SYSTEM

The present invention relates to a drug delivery system. More particularly, it relates to a system in which a drug is intercalated into a layered double hydroxide.

Layered double hydroxides (LDHs) are a class of compounds which comprise two metal cations and have a layered structure. A brief review of LDHs is provided in *Chemistry in Britain*, September 1997, pages 59 to 62. The hydrotalcites, perhaps the most well-known examples of LDHs, have been studied for many years.

LDHs can be represented by the general formula $[M^{II}_{(1-x)}M^{III}_x(OH)_2]^{x+}A^{z-}_{x/z}.yH_2O$ or $[M^I_{(1-x)}M^{III}_x(OH)_2]^{n+}A^{z-}_{n/z}.yH_2O$, where $M^I$, $M^{II}$ and $M^{III}$ are mono, di- and trivalent metal cations respectively, that occupy octahedral positions in hydroxide layers, $A^{z-}$ is an interlayer charge-compensating anion where z is an integer, such as $CO_3^{2-}$, $NO_3^-$ or $Cl^-$, n=2x−1, x is a number less than 1 and y is 0 or a number greater than 0. A large number of LDHs with a wide variety of $M^{II}$-$M^{III}$ cation pairs (e.g., Ca—Al) as well as the $M^I$-$M^{III}$ cation pair (Li—Al) with different anions in the interlayer space have been reported and studied.

It is known that certain organic species may be intercalated into the layers in some LDHs and into days. For example, Ogawa et al., in *Chemistry Letters*, 1992, no. 3, p. 365-368, describe the intercalation of maleic and methylmaleic acids into the clay montmorillonite in a solid state reaction. The geometrical isomers of the acids, fumaric and methylfumaric acids, were not intercalated in the solid state reaction. However, when an ethanolic solution of the two isomers was used, the montmorillonite showed no selectivity and both isomers were intercalated.

The structure of the layered materials $[LiAl_2(OH)_6]X$, where X is Cl, Br or $NO_3$, and their hydrates has been described by Besserguenev at al., in *Chem. Mater,* 1997, no. 9, p. 241-247. The materials can be produced by the reaction of gibbsite $[\gamma\text{-Al(OH)}_3]$ or other forms of $Al(OH)_3$, such as bayerite, nordstrandite or doyleite, with lithium salts of formula LiX. The materials can also be formed in other ways, such as by direct precipitation (see, for example, Serna et al., *Clays & Clay Minerals*, (1997), 25, 384). The structure of the $LiAl_2(OH)_6^+$ layers in the compounds is unusual amongst LDHs since it is based on an ordered arrangement of metal cations within the layers.

The synthesis of $LiAl_2(OH)_6^+$ compounds is described in U.S. Pat. No. 4,348,295 and U.S. Pat. No. 4,348,297. The use of the materials for separating hydrocarbons and for gas chromatograph columns is taught in U.S. Pat. No. 4,430,097 and U.S. Pat. No. 4,321,065, respectively. In both of these latter two documents, the technology described does not involve intercalation chemistry but surface interactions with the stationary phase i.e., liquid-solid or gas-solid interactions.

Intercalates of compounds of formula $LiOH.2Al(OH)_3$ are described in U.S. Pat. No. 4,727,167 and U.S. Pat. No. 4,812,245. Both documents relate to uses of the intercalates as additives to organic materials such as mineral oils.

A few other LDHs having cation ordering are known. The layered double hydroxide $[Ca_2Al(OH)_6]_2^+SO_4^{2-}$ is an example.

LDHs exhibit a wide range of anion-exchange reactions with guests such as organic carboxylates, sulfonates and a range of anionic metal complexes. These materials are of significant technological importance in diverse areas such as catalysis, optics, medical science and separation science.

The application of LDHs in separation science has until recently been largely restricted to their role as fast, efficient, high capacity ion-exchange materials. The major application being the removal of organic and inorganic anions from aqueous streams. According to WO 99/24139 a compound comprising at least two negatively charged groups connected by a linker group can be separated from a mixture containing it by selectively intercalating it into an LDH. For example, it was disclosed therein that when $[LiAl_2(OH)_6]Cl.H_2O$ is treated with an equimolar mixture of the disodium salts of either the 1,2-, 1,3- or 1,4-dibenzoic acids then the only crystalline phase observed is formed by preferential and exclusive intercalation of the 1,4-dibenzoate anions.

Choy et al., J. Am. Chem. Soc. 1999, 121, 1399-1400, have reported that the nucleoside monophosphates such as adenosine-5'-monophosphate (AMP), guanosine-5'-monophosphate (GMP) and cytidine-5'-monophosphate (CMP) can be ion-exchange intercalated in the layered double hydroxide $[Mg_{0.68}Al_{0.32}(OH)_2](NO_3)_{0.32}.1.2H_2O$.

BRIEF DESCRIPTION OF THE DRAWINGS

The release profiles for diclofenac at pH 4 and pH 7 are shown in FIG. 1.

The release profiles for Naproxen at pH 4 and pH 7 are shown in FIG. 2.

Figure 3:
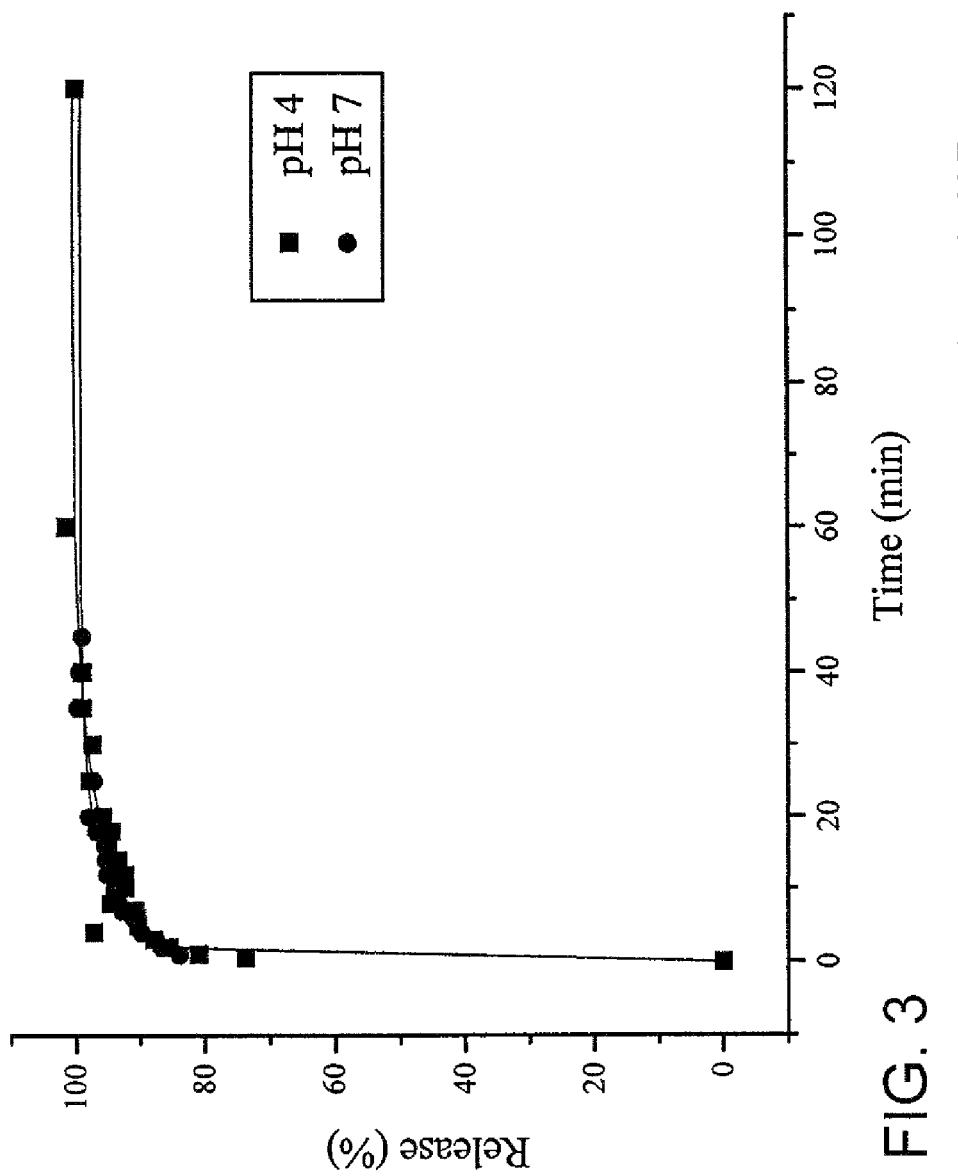

The release profiles for Gemfibrozil at pH 4 and pH 7 are shown in FIG. 3.

Figure 4:
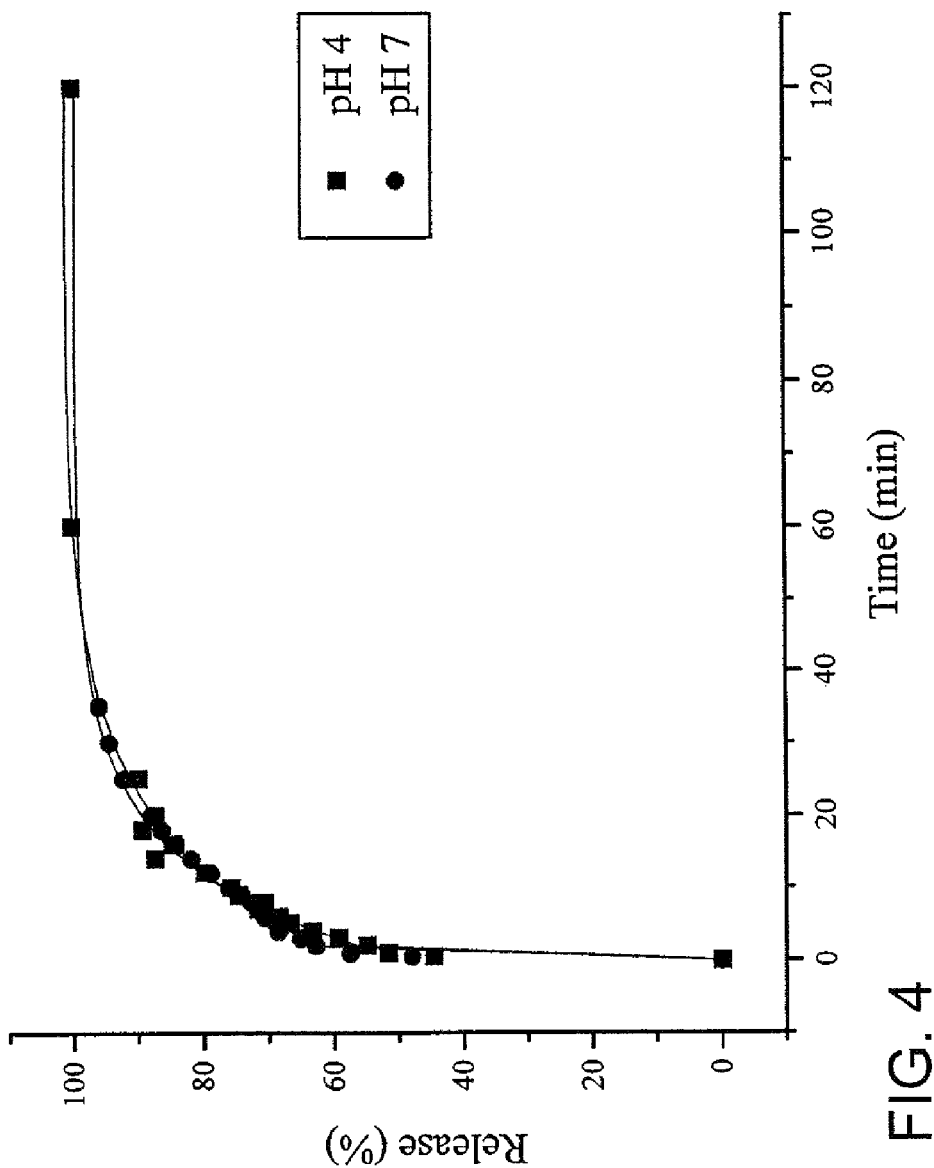

The release profiles for Tolfenamic acid at pH 4 and pH 7 are shown in FIG. 4.

Figure 5:
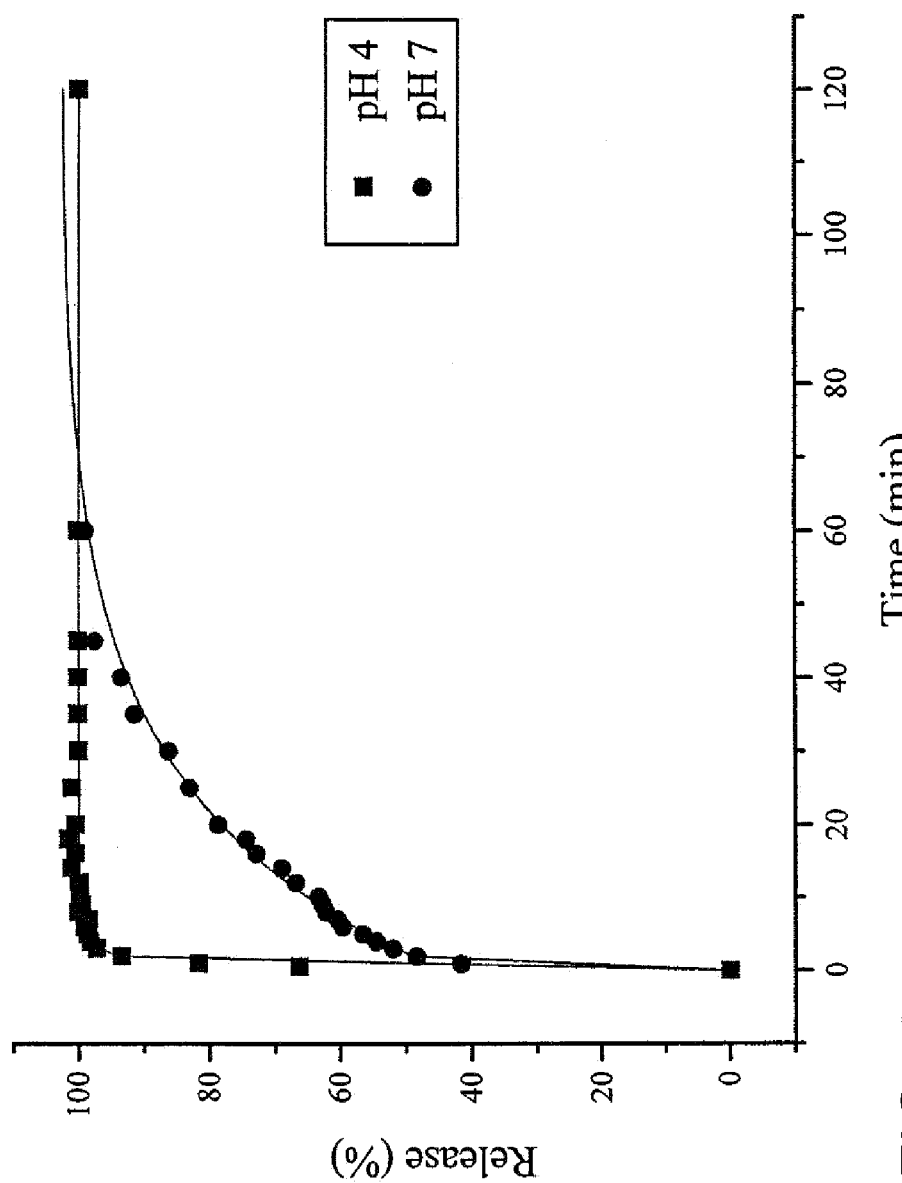

The release profiles for 4-biphenylacetic acid at pH 4 and pH 7 are shown in FIG. 5.

Figure 6:
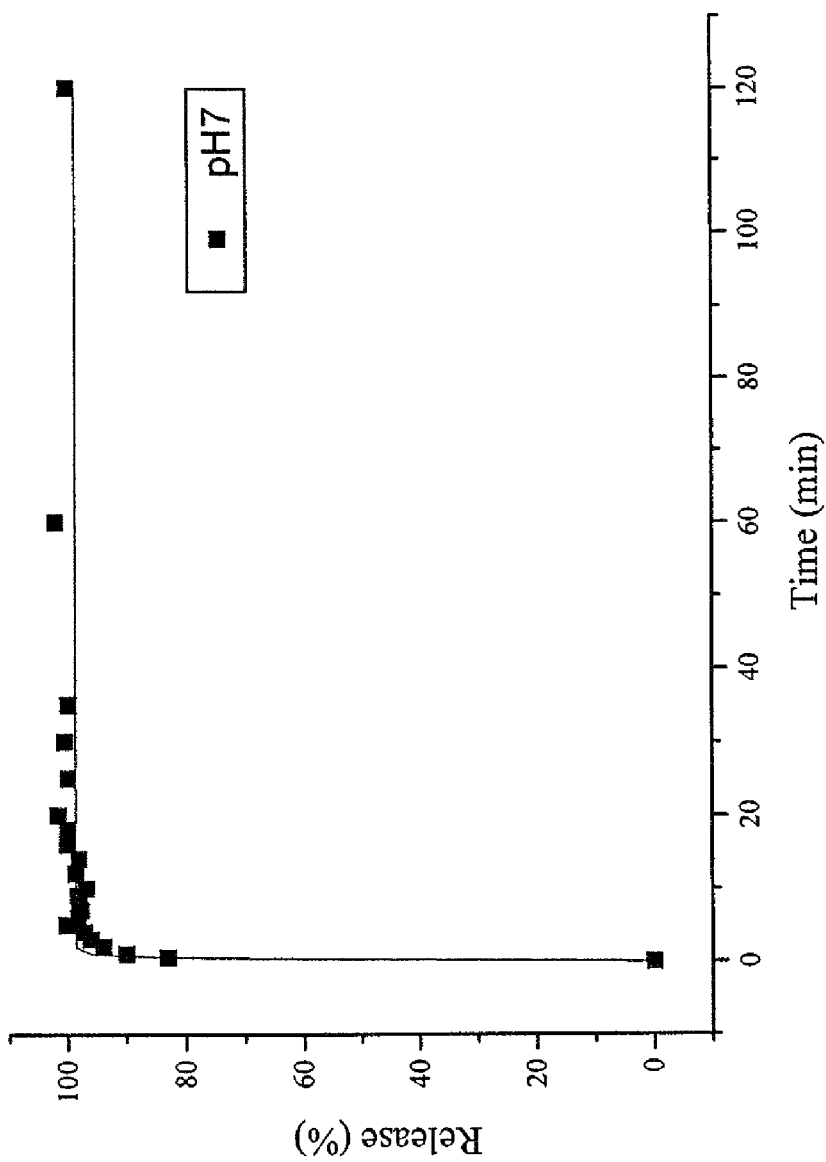

The release profile of Naproxen from its intercalation compound at pH 7 is shown in FIG. 6.

The present invention provides a drug delivery system comprising an intercalate of a layered double hydroxide having, before intercalation, layers of metal hydroxides and having intercalated therein a pharmaceutically-active compound having at least one anionic group.

The present invention is based on the discovery that a pharmaceutically-active compound having at least one anionic group can be intercalated into an LDH compound and that the intercalate releases the pharmaceutically-active compound in a controlled manner when subjected to pH conditions that may prevail inside the stomach of a patient. It is known that certain pharmaceutically-active compounds, when administered orally, may cause irritation of the stomach. Some patients are, of course, more vulnerable to irritation of this kind than others. By controlling the release of such compounds in the stomach such a side-effect can be avoided or, at least, reduced.

The layered double hydroxide that can be used in the drug delivery system of the invention comprises two metal cations and hydroxide ions and has a layered structure. Between the layers, the LDH contains an intercalated anionic group which is one that can be displaced by the pharmaceutically-active compound.

A first, preferred, class of LDH compounds that can be used in the manufacture of the drug delivery system of the invention has the general formula I

$$[M^I M_2^{III}(OH)_6]^+[A_{1/n}{}^{n-}] \tag{I}$$

in which $M^I$ is a monovalent metal cation, $M^{III}$ is a trivalent metal cation, A is a displaceable anion and n is an integer. These compounds are optionally, but preferably, hydrated. The amount of water of hydration may be a stoichiometric amount or a non-stoichiometric amount. Of this class of LDH compounds, those wherein $M^I$ is a lithium ion and $M^{III}$ is an aluminium ion are particularly preferred such that the layers in the compound comprise $[LiAl_2(OH)_6]^+$. The cations in such a layer have an ordered arrangement, i.e., the LDH has cation ordering. The ordered (i.e., non-random) arrangement of cations is believed to be beneficial and to enhance the intercalation of the pharmaceutically-active compound in the system of the invention.

In the above formula I the anion A is one that can be displaced from its location between the metal cation-containing layers in the LDH by the pharmaceutically-active compound. For example, it may be an anion selected from hydroxide, halide (i.e., fluoride, chloride, bromide or iodide), sulfate or nitrate ions. Preferably, the anion A is chloride or nitrate.

A second, preferred, class of LDH compound that can be used in the manufacture of the drug delivery system of the invention has the general formula II

  (II)

in which $M^{II}$ is a divalent metal cation, for example, $Ca^{2+}$, $Mg^{2+}$, $Zn^{2+}$ and $Ni^{2+}$ ions, $M^{III}$ is a trivalent metal cation, for example $Al^{3+}$ and $Fe^{3+}$ ions, A is a displaceable anionic group such as one disclosed above in connection with the described first class of LDH compounds, n is an integer and x is a number less than 1. Such compounds are optionally, but preferably, hydrated. The water of hydration, if present, may be present in a stoichiometric amount or a non-stoichiometric amount.

A preferred LDH compound for use in preparing the drug delivery system of the invention is $[LiAl_2(OH)_6]Cl.H_2O$.

The drug delivery system of the invention comprises an LDH in which is intercalated a pharmaceutically-active compound having at least one anionic group. The pharmaceutically-active compound may be any compound which may have use in the treatment of any disease, disorder or condition in the body of an animal, including human, provided that the compound has activity when administered by an oral route and provided that it has at least one anionic group which will enable it to intercalate into the LDH to displace the anion A from the initial LDH compound. Thus, provided that the above requirements are met the pharmaceutically-active compound may be a drug, a pro-drug or drug precursor or a substance for treating a treatable disorder or condition of the animal body, including the human body. Such active compounds have at least one anionic group, for example a carboxylic acid group or a non-toxic metal or ammonium salt thereof. Examples of pharmaceutically-active compounds that may be intercalated into an LDH to form an intercalation compound having use as a drug delivery system according to the invention include, but are not limited to, 4-biphenylacetic acid, sodium (2-(2,6-dichloroanilino)phenyl)acetate (Diclofenac Sodium), 2,2-dimethyl-5-(2,5-xylyloxy)valeric acid (Gemfibrozil), 2-(4-isobutylphenyl)propionic acid (Ibuprofen), (+)-2-(6-methoxy-2-naphthyl)propionic acid (Naproxen), 2-propylpentanoic acid and N-(3-chloro-o-tolyl) anthranilic acid (Tolfenamic acid).

In order to effect intercalation, an aqueous solution of the pharmaceutically-active compound, optionally in the form of a non-toxic salt thereof, is treated with the layered double hydroxide and then the intercalate compound, so formed, is separated from the reaction mixture. Typically, the treatment will be performed by, firstly, preparing an aqueous suspension of the LDH compound and then mixing this with an aqueous solution of the pharmaceutically-active compound (or a non-toxic salt thereof). Preferably, an aqueous suspension of the LDH is treated by ultrasonication for a period of time of from 1 to 60 minutes, more preferably from 30 to 45 minutes, prior to mixing this with the solution containing the pharmaceutically-active compound, since this prior sonication treatment enhances the extent of the intercalation reaction. Typically, the intercalation reaction is carried out by stirring the aqueous mixture of the reactants for a period of time within the range of from 2 to 72 hours. The pharmaceutically-active compound in the solution treated with the LDH will preferably be in a molar excess with respect to the LDH. Typically, the molar ratio of pharmaceutically-active compound to LDH will be at least 2:1 since such guest:host ratios promote a greater extent of intercalation. The temperature of the reaction mixture will typically be held at at least 30° C. for at least part of the reaction period. Whereas Naproxen is intercalated into the LDH after a reaction time of 1 to 2 days at 30° C., the reaction of Tolfenamic acid with the LDH requires a longer period of time and a higher reaction temperature, typically about 3 days at a temperature of about 80° C.

After the intercalation reaction, the particles of the LDH containing intercalated pharmaceutically-active compound are separated from the aqueous medium, for instance by filtration.

The separated LDH particles containing the intercalated pharmaceutically-active compound will then be dried prior to formulation into the required oral dosage units.

The intercalate compounds have been found to release the pharmaceutically-active compound in a controlled manner when subjected to an acid environment similar to that which exists in the stomach of an animal (including a human). This is because the LDH is broken down by treatment with a dilute acid, such as hydrochloric acid. LDH compounds, themselves, are known to have an antacid effect. Thus, an intercalate of the invention when administered orally to a patient has the effect of altering the pH of the environment inside the stomach of the patient which, in turn, affects the breakdown of the intercalate and, therefore, the rate of release of the pharmaceutically-active compound from the intercalate. Since the rate of breakdown of the intercalate in the stomach and the degree of antacid effect depends on the chemical nature of the lattice of the LDH used it is possible to control or modify the rate of release of the pharmaceutically-active compound from the intercalate by an appropriate selection of the host lattice used in the manufacture of the intercalate. The pH of the contents of the stomach can also be controlled by the addition of a buffer, for instance, a phosphate buffer. Thus, the incorporation of a buffer into a formulation, which includes the intercalate containing the pharmaceutically-active compound, to be administered to a patient allows the pH to be fine tuned to optimise the rate of breakdown of the LDH lattice and, thus, the rate of release of the pharmaceutically-active compound from the intercalate. According to a different embodiment, it may be advantageous to include, with the intercalate compound in the formulation to be administered to a patient, a non-toxic compound which contains an anion that intercalates between the layers in the LDH in preference to the pharmaceutically-active compound. By providing such a compound, the release of the pharmaceutically-active compound in the patient's stomach is promoted by the action of the anion to displace the pharmaceutically-active compound from the layers in the LDH. Suitable anions for this purpose include carbonate and hydrogen carbonate anions although anions, which intercalate more or less strongly than carbonate can be used. A carbonate compound is, however, preferred on account of the strong capacity of carbonate anion to bind with the LDH and displace the guest pharmaceutically-active compound from the LDH. Examples of suitable non-toxic carbonate and hydrogen carbonate compounds that can be used in this embodiment of the invention include $CaCO_3$, $Ca(HCO_3)_2$, $MgCO_3$ and $Mg(HCO_3)_2$.

EXAMPLES

Example 1

Intercalation of Pharmaceutically-Active Compounds in $[LiAl_2(OH)_6]Cl.H_2O$ Table 1 lists pharmaceutically-active compounds which we have intercalated into a layered double hydroxide (LDH) host of formula $[LiAl_2(OH)_6]Cl.H_2O$. The intercalation of the drug was achieved by adding 1.4 mmol of the sodium salt of the drug in 10 ml of deionised $H_2O$ to a suspension of 0.7 mmol of the host in 10 ml of deionised $H_2O$. The suspension of the host was sonicated for 30 minutes prior to the addition of the sodium salt of the drug. The mixture was then stirred in a sealed glass ampoule for 1-2 days at a temperature of 30° C.

4-Biphenylacetic acid and Tolfenamic acid are anti-inflammatory and analgesic agents. Diclofenac is used for the treatment of arthritis, ibuprofen and naproxen are both non-steroidal anti-inflammatory agents. Gemfibrozil is a lipid regulating agent and 2-propylpentanoic acid inhibits GABA transaminase.

TABLE 1

Summary of the guest molecule used and the analytical and structural data of the LDH-drug intercalation compounds.

| Guest | Molecular Structure of Guest[a] | Interlayer Spacing/ Å[b] | Elemental Analysis Found (calc)[c] |
|---|---|---|---|
| 4-Biphenylacetic acid $C_{14}H_{12}O_2$ | | 20.4 | C 30.77 (30.77) H 5.16 (5.20) x = 0.58, y = 2 |
| Diclofenac $C_{14}H_{10}Cl_2NaNO_2$ | | 22.3 | C 30.91 (30.92) H 4.12 (3.91) N 2.60 (2.58) x = 0.72, y = 1. |
| Gemfibrozil $C_{15}H_{22}O_3$ | | 23.2 | C 35.35 (35.36) H 6.56 (6.65) x = 0.69, y = 1 |
| Ibuprofen $C_{13}H_{18}O_2$ | | 22.7 | C 31.92 (31.98) H 6.15 (5.99) x = 0.75, y = 3 |
| Naproxen $C_{14}H_{14}O_3$ | | 21.5 | C 27.91 (28.08) H 4.98 (4.99) x = 0.48, y = 1 |
| 2-Propylpentanoic acid $C_8H_{16}O_2$ | | 18.7 | C 14.78 (14.82) H 5.77 (6.04) x = 0.35, y = 1 |

TABLE 1-continued

Summary of the guest molecule used and the analytical and structural data of the LDH-drug intercalation compounds.

| Guest | Molecular Structure of Guest[a] | Interlayer Spacing/ Å[b] | Elemental Analysis Found (calc)[c] |
|---|---|---|---|
| Tolfenamic acid $C_{14}H_{12}ClNO_2$ | (structure) | 21.9 | C 23.24 (23.18) H 5.25 (5.29) N 1.90 (1.93) x = 0.46, y = 3 |

[a]Neutral guest molecules were converted to the sodium salt prior to intercalation.
[b]Based on hexagonal cell $\alpha = \beta = 90°$, $\gamma = 120°$, a = b = 5.1 Å, and c = 2 × $d_{(002)}$
[c]Based on the general formula formula $Li_xAl_2(OH)_6[drug]_x \cdot yH_2O$ Methods of Recovery/Release of the Drugs from the Solid Host.

All of the above drugs have been quantitatively exchanged back out of the host LDH, for example, by using one of the following procedures:

1. Addition of carbonate; adding 0.113 g of $Na_2CO_3$ to approx. 0.100 g of the intercalation compound in 8 ml of $D_2O$ and stirring overnight in a sealed glass ampoule.
2. Addition of acid; All the intercalation compounds react with 0.2M HCl to produce the neutral drug molecule.
3. Addition of phosphate buffer (ca. pH7).

NMR spectra and XRD patterns were measured to confirm the release of the drugs.

Example 2

Intercalation compounds were obtained by intercalating the pharmaceutically-active compounds described in Example 1 into $[LiAl_2(OH)_6]Cl \cdot H_2O$ according to the procedure of Example 1.

Release of the drugs from their intercalation compounds was performed in each case by the addition of 0.0250 g-0.100 g of the intercalation compound to 250 mL phosphate buffer solution at 37° C. (body temperature) in a round bottom flask and the mixture stirred at 1000 rpm. The release in phosphate buffer at pH 7 and at pH 4 was investigated. Aliquots were removed from the flask at regular time intervals, the solution was filtered and the UV spectrum of the filtrate recorded in a 1 $cm^2$ quartz cuvette. A baseline scan using the neat solution was recorded prior to the collection of the first spectrum of the filtrate.

Figure 1:
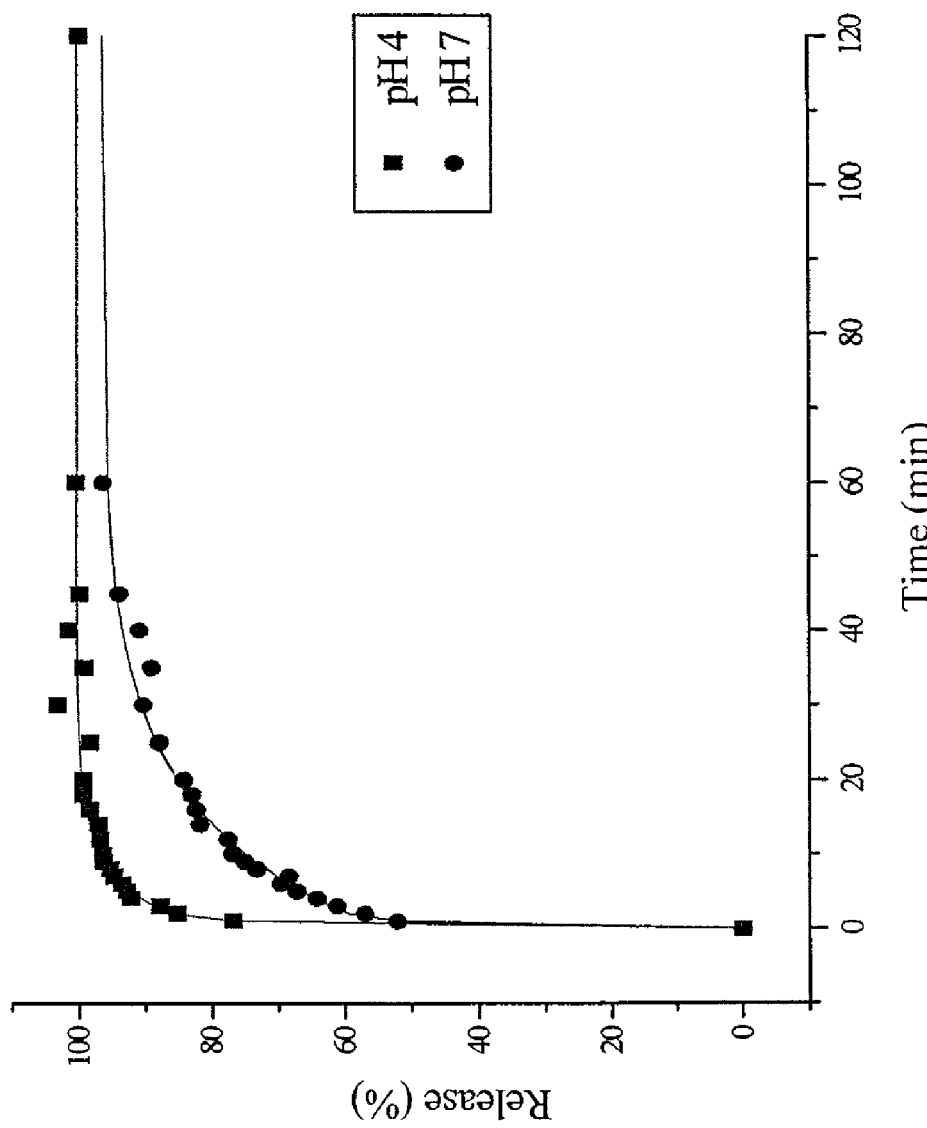
Figure 2:
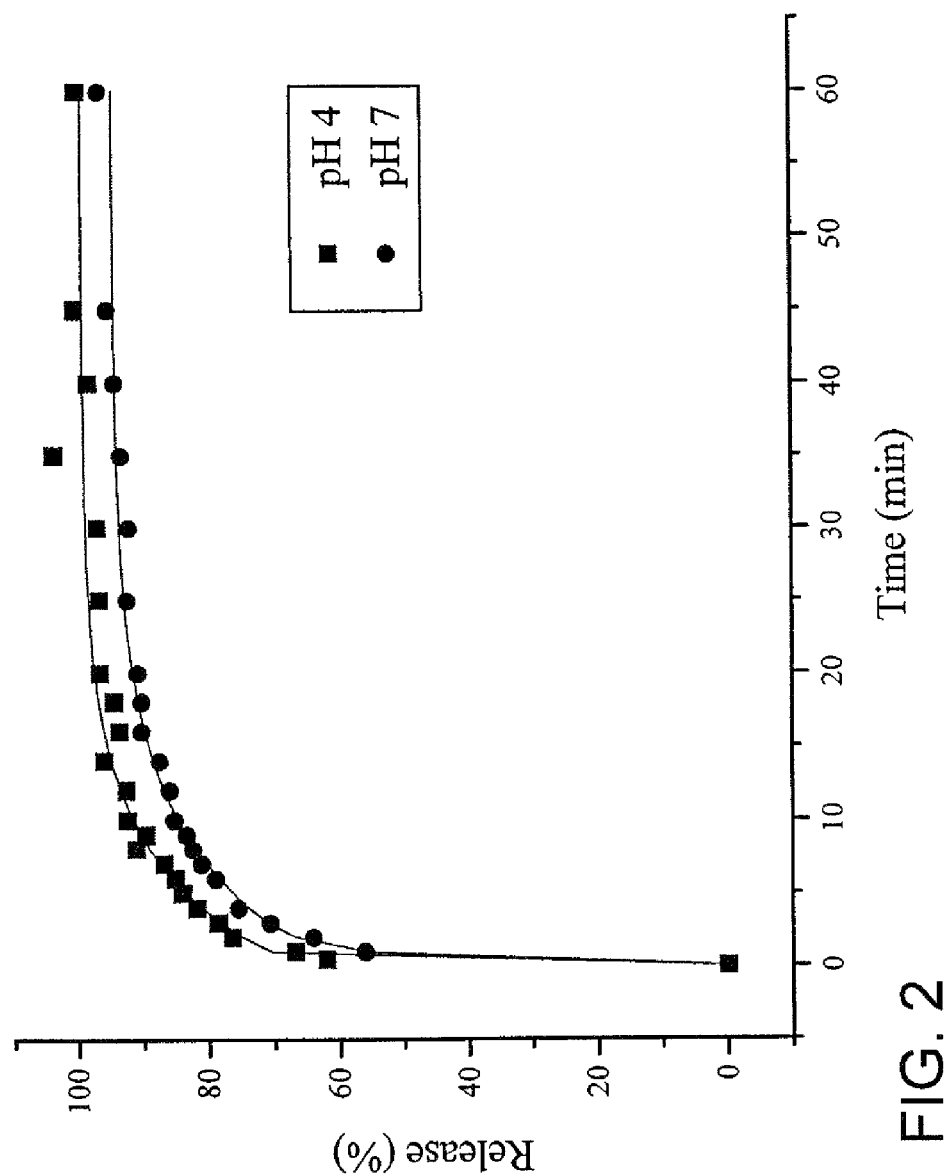

The release profiles for diclofenac at pH 4 and pH 7 are shown in FIG. 1. The release profiles for Naproxen at pH 4 and pH 7 are shown in FIG. 2. The release profiles for Gemfibrozil at pH 4 and pH 7 are shown in FIG. 3. The release profiles for Tolfenamic acid at pH 4 and pH 7 are shown in FIG. 4. The release profiles for 4-biphenylacetic acid at pH 4 and pH 7 are shown in FIG. 5.

The release of Diclofenac (FIG. 1), Naproxen (FIG. 2) and 4-biphenylacetic acid (FIG. 5) was rapid at pH 4 but was slower and more controlled at pH 7.

Example 3

Intercalation of Pharmaceutically-Active Compounds in $[Ca_2Al(OH)_6]NO_3 \cdot xH_2O$ Intercalation of the pharmaceutically-active compounds was achieved by the addition of 1.4 mmol of the sodium salt of the drug in 10 ml deionised $H_2O$ to 0.7 mmol of the LDH host of formula $[Ca_2Al(OH)_6]NO_3 \cdot xH_2O$. The mixture was then stirred in a sealed glass ampoule for 18 hours at a temperature of 80° C. The solid products were isolated by filtration and washed with an excess of deionised water and acetone and allowed to dry in air. The formulae and d-spacings of the intercalation compounds synthesised are listed in the following Table 2.

TABLE 2

| Drug Molecule | Intercalation Compound | d-spacing Å |
|---|---|---|
| 4-Biphenylacetic acid $C_{14}H_{12}O_2$ | $[Ca_{1.875}Al(OH)_6][C_{14}H_{11}O_2]_{0.75} \cdot 2H_2O$ | 19.5 |
| Diclofenac $C_{14}H_{10}Cl_2NaNO_2$ | $[Ca_{1.9}Al(OH)_6][C_{14}H_{10}Cl_2NO_2]_{0.8} \cdot 2H_2O$ | 22.4 |
| Gemfibrozil $C_{15}H_{22}O_3$ | $[Ca_{1.825}Al(OH)_6][C_{15}H_{21}O_3]_{0.65} \cdot H_2O$ | 22.5 |
| Ibuprofen $C_{13}H_{18}O_2$ | $[Ca_{1.9}Al(OH)_6][C_{13}H_{17}O_2]_{0.8} \cdot H_2O$ | 19.8 |
| Naproxen $C_{14}H_{14}O_3$ | $[Ca_2Al(OH)_6][C_{14}H_{13}O_3]_{0.63} \cdot 3H_2O$ | 19.7 |
| Tolfenamic acid $C_{14}H_{12}ClNO_2$ | $[Ca_{1.75}Al(OH)_6][C_{14}H_{11}ClNO_2]_{0.5} \cdot 2H_2O$* | 19.8 |

*In order to achieve the intercalation of tolfenamic acid the mixture was heated at a temperature of 80° C. for approx. 3 days.

Release of Naproxen was performed and investigated as described in Example 2. The release profile of Naproxen from its intercalation compound at pH 7 is shown in FIG. 6.

Example 4

Intercalation of Pharmaceutically-Active Compounds in $[Mg_2Al(OH)_6]NO_3 \cdot H_2O$ Intercalation of the drug molecules listed in Table 2 was achieved by the addition of 1.4 mmol of the sodium salt of the drug in 10 ml deionised $H_2O$ to 0.7 mmol of the LDH host of formula $[Mg_2Al(OH)_6]NO_3.H_2O$. The mixture was then stirred in a seated glass ampoule for 12 hours at a temperature of 60° C. The solid products were isolated by filtration and washed with an excess of deionised water and acetone and allowed to dry in air.

The invention claimed is:

1. A method comprising:
   orally administering to a subject a formulation comprising:
   a drug delivery system comprising an intercalate of a layered double hydroxide having, before intercalation, layers of metal hydroxides, and having intercalated therein a pharmaceutically-active compound having at least one anionic group; and
   a non-toxic compound comprising an anion configured to intercalate between the layers in the layered double hydroxide in preference to the pharmaceutically-active compound and release the pharmaceutically-active compound in the subject's stomach by displacing the pharmaceutically-active compound from the layers in the layered double hydroxide.

2. The method according to claim 1, wherein the layered double hydroxide, before intercalation, is represented by the general formula:

$$[M^{II}_{(1-x)}M^{III}_x(OH)_2]^{x+}[A^{n-}_{x/n}]$$

wherein:
M$^{II}$ is a divalent metal cation;
M$^{III}$ a trivalent metal cation;
A is a displaceable anion;
n is an integer; and
x is a positive number less than 1, which compound is optionally hydrated with a stoichiometric amount or a non-stoichiometric amount of water.

3. The method according to claim 2, wherein M$^{II}$ is Mg or Ca and M$^{III}$ is Al.

4. The method according to claim 2, wherein A is selected from the group consisting of OH, F, Cl, Br, I, $SO_4$, and $NO_3$.

5. The method according to claim 1, wherein the layered double hydroxide, before intercalation, is represented by the general formula:

$$[M^IM^{III}_2(OH)_6]^+[A^{n-}_{1/n}]$$

wherein:
M$^I$ is a monovalent metal cation;
M$^{III}$ a trivalent metal cation;
A is a displaceable anion; and
n is an integer, which compound is optionally hydrated with a stoichiometric or non-stoichiometric amount of water.

6. The method according to claim 5, wherein M$^I$ is Li and M$^{III}$ is Al.

7. The method according to claim 5, wherein A is selected from the group consisting of OH, F, Cl, Br, I, $SO_4$, and $NO_3$.

8. The method according to claim 7, wherein the layered double hydroxide is $[LiAl_2(OH)]_6Cl.H_2O$.

9. The method according to claim 1, wherein the pharmaceutically-active compound is a pharmaceutically-active compound containing at least one carboxylic acid group or a non-toxic salt thereof.

10. The method according to claim 1, wherein the intercalate further comprises a non-toxic compound having an anion which is capable of displacing the pharmaceutically-active compound from the intercalate.

11. The method according to claim 10, wherein the non-toxic compound is selected from the group consisting of magnesium carbonate, magnesium hydrogen carbonate, calcium carbonate or calcium hydrogen carbonate.

12. The method according to claim 1, wherein the pharmaceutically-active compound is selected from the group consisting of 4-biphenylacetic acid, Diclofenac, Gemfibrozil, Ibuprofen, Naproxen, 2-propylpentanoic acid and Tolfenamic acid.

13. The method according to claim 1, wherein the intercalate is configured to release the pharmaceutically-active compound in a controlled manner over a period of time.

14. The method according to claim 13, wherein the period of time is 120 minutes or less.

15. The method according to claim 1, wherein the drug delivery system is an oral dosage unit.

16. The method according to claim 1, wherein the drug delivery system comprises a buffer.

17. The method according to claim 16, wherein the buffer comprises a phosphate buffer.

18. The method according to claim 1, wherein the anion of the non-toxic compound is a carbonate anion or a hydrogen carbonate anion.

19. The method according to claim 1, wherein the anion of the non-toxic compound is an anion which intercalates more strongly than a carbonate anion.

20. The method according to claim 1, wherein the anion of the non-toxic compound is an anion which intercalates less strongly than a carbonate anion.

* * * * *